United States Patent [19]

King

[11] Patent Number: 4,918,079

[45] Date of Patent: Apr. 17, 1990

[54] IMIDAZOLE DERIVATIVES AS 5-HT$_3$ RECEPTOR ANTAGONISTS

[75] Inventor: Francis D. King, Harlow, England

[73] Assignee: Beecham Group p.l.c., Brentford, England

[21] Appl. No.: 252,373

[22] Filed: Sep. 30, 1988

[30] Foreign Application Priority Data

Oct. 2, 1987 [GB] United Kingdom ............... 8723157

[51] Int. Cl.$^4$ ............... A61K 31/44; A61K 31/415; C07D 403/06; C07D 471/04
[52] U.S. Cl. .......................... 514/299; 514/397; 514/400; 546/112; 546/183; 548/336; 548/342
[58] Field of Search ............. 548/336, 337, 342; 514/397, 400, 299; 546/112, 183

[56] References Cited

U.S. PATENT DOCUMENTS

| | | | |
|---|---|---|---|
| 4,622,336 | 11/1986 | Achini | 548/311 X |
| 4,720,551 | 1/1988 | Fujita et al. | 548/336 X |
| 4,772,613 | 9/1988 | Parsons et al. | 548/336 X |
| 4,808,581 | 2/1989 | Oxford et al. | 548/336 X |
| 4,814,344 | 3/1989 | Humber et al. | 548/336 X |

FOREIGN PATENT DOCUMENTS

| | | |
|---|---|---|
| 200444 | 11/1986 | European Pat. Off. . |
| 235878 | 9/1987 | European Pat. Off. . |
| 242973 | 10/1987 | European Pat. Off. . |
| 247266 | 12/1987 | European Pat. Off. . |
| 266899 | 5/1988 | European Pat. Off. . |
| 276163 | 7/1988 | European Pat. Off. . |
| 2045244 | 10/1980 | United Kingdom . |
| 2125398 | 3/1984 | United Kingdom . |
| 2153821 | 8/1986 | United Kingdom . |

OTHER PUBLICATIONS

J. Fozard in *The Peripheral Actions of 5-Hydroxy-Tryptamine*, (J. Fozard, Editor), Oxford Univ. Press, Oxford, 1989, pp. 354–376.
Ch. Ab. 109:104602h, 1988, Scheinen et al.
Ch. Abs. 108(17):150475, 1988, Karjalainen et al.

Primary Examiner—Richard A. Schwartz
Attorney, Agent, or Firm—Hopgood, Calimafde, Kalil, Blaustein & Judlowe

[57] ABSTRACT

Compounds of formula (I) and pharmaceutically acceptable salts thereof:

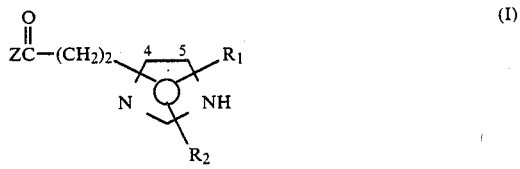

wherein the various substituents are defined hereinbelow, having 5-HT$_3$ receptor antagonist activity, processes for their preparation and their use as pharmaceuticals.

8 Claims, No Drawings

IMIDAZOLE DERIVATIVES AS 5-HT$_3$ RECEPTOR ANTAGONISTS

This invention relates to novel compounds having useful pharmacological properties, to pharmaceutical compositions containing them, to a process and intermediates for their preparation, and to their use as pharmaceuticals.

EP-A-242973 discloses a class of indole derivatives which are 5-HT$_3$ receptor antagonists.

A class of novel, structurally distinct compounds has now been discovered which compounds have 5-HT$_3$ receptor antagonist activity.

Accordingly, the present invention provides a compound of formula (I), or a pharmaceutically acceptable salt thereof:

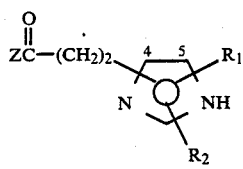

wherein $R_1$ and $R_2$ are independently hydrogen or $C_{1-6}$ alkyl;
Z is a group of sub-formula (a), (b), (c), (d) or (e):

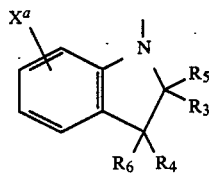 (a)

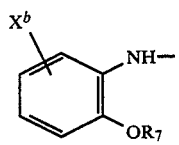 (b)

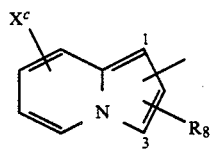 (c)

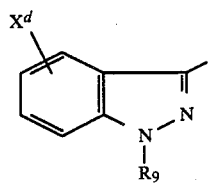 (d)

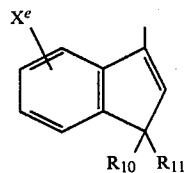 (e)

wherein $X^a$ to $X^3$ are selected from hydrogen, halogen and hydroxy;
$R_3$ is hydrogen and $R_4$ is hydrogen or $C_{1-6}$ alkyl, or $R_3$ and $R_4$ together are a bond;
$R_5$ to $R_{11}$ are independently selected from hydrogen or $C_{1-6}$ alkyl; and $R_6$ together with $R_4$ may be $C_{2-7}$ polymethylene when $R_3$ is hydrogen, or $R_{10}$ and $R_{11}$ may together be $C_{2-7}$ polymethylene.

Examples of moieties in alkyl or alkyl containing groups in $R_1$, $R_2$ and $R_4$ to $R_{11}$ include methyl, ethyl, n- and iso-propyl, n-, iso-, sec- and tert-butyl, preferably methyl.

Suitable examples of $R_4$ and $R_6$ or $R_{10}$ and $R_{11}$ when joined include $C_2$, $C_3$, $C_4$, $C_5$ or $C_6$ polymethylene, preferably $C_2$, $C_3$, $C_4$ or $C_5$ polymethylene.

$X^a$ to $X^e$ are preferably selected from hydrogen, fluoro, chloro and hydroxy, most preferably hydrogen.

Preferably the ZCO—(CH$_2$)$_2$— moiety is attached to the imidazole ring at the 4-position. Preferably $R_1$ is hydrogen or methyl, attached at the 5-position and $R_2$ is hydrogen.

When Z is of sub-formula (a), $R_3$ and $R_5$ are preferably both hydrogen and one or both $R_4$ and $R_6$ (most preferably both) are alkyl groups, such as methyl, or are joined to form $C_{2-7}$ polymethylene.

When Z is of sub-formula (b), $R_7$ is preferably methyl.

When Z is of sub-formula (c), one of CO—(CH$_2$)$_2$— and $R_8$ is attached to the 1-position and the other is attached at the 3-position as depicted in sub-formula (C), and $R_8$ is preferably methyl or ethyl.

When Z is of sub-formula (d), $R_9$ is preferably hydrogen or a methyl or ethyl group.

When Z is of sub-formula (e), one or both of $R_{10}$ and $R_{11}$ (most preferably both) are alkyl groups, such as methyl or are joined to form $C_{2-7}$ polymethylene.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, lactic, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, lactic and acetic acid.

Preferably the acid addition salt is the hydrochloride salt.

Examples of pharmaceutically acceptable salts include quaternary derivatives of the compounds of formula (I) such as the compounds quaternised by compounds $R_a$-T wherein $R_a$ is $C_{1-6}$ alkyl, phenyl-$C_{1-6}$ alkyl or $C_{5-7}$ cycloalkyl, and T is a radical corresponding to an anion of an acid. Suitable examples of $R_a$ include methyl, ethyl and n- and iso-propyl; and benzyl and phenethyl. Suitable examples of T include halide such as chloride, bromide and iodide.

Examples of pharmaceutically acceptable salts of compounds of formula (I) also include internal salts such as pharmaceutically acceptable N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

It will of course be realised that some of the compounds of the formula (I) have chiral or prochiral centres and thus are capable of existing in a number of stereoisomeric forms including enantiomers. The invention extends to each of these stereoisomeric forms (including enantiomers), and to mixtures thereof including racemates. The different stereoisomeric forms may be separated one from another by the usual methods.

It will be appreciated that the imidazole ring in formula (I) can exist as tautomers i.e. the hydrogen atom can be on either of the imidazole nitrogen atoms. The invention extends to both tautomers and mixtures thereof.

The invention provides process for the preparation of a compound of formula (I) wherein Z is of formula (a) or (b), or a pharmaceutically acceptable salt thereof, which process comprises reacting a compound of formula (II):

TI Z¹H  (II)

wherein $Z^1$ is of sub-formula (a) or (b), with a compound of formula (III):

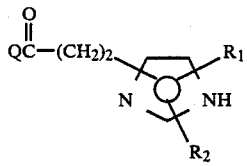  (III)

wherein Q is a leaving group and the remaining variables are as defined in formula (I); and thereafter optionally forming a pharmaceutically acceptable salt thereof.

Examples of leaving groups Q, displaceable by a nucleophile, including halogen such as chloro and bromo; $C_{1-4}$ alkoxy, such as $CH_3O$ and $C_2H_5O$—; PhO—; activated hydrocarbyloxy, such as $Cl_5C_6O$— or $Cl_3CO$—; succinimidyloxy; and imidazolyl. Preferably Q is halogen, most preferably chloro.

If a group Q is a halide or imidazolyl, then the reaction is preferably carried out at non-extreme temperatures in an inert non-hydroxylic solvent, such as benzene, dichloromethane, toluene, diethyl ether, tetrahydrofuran (THF) or dimethylformamide (DMF). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°–100° C., in particular 10°–80° C. are suitable.

If a group Q is $C_{1-4}$ alkoxy, phenoxy, activated hydrocarbyloxy or succinimidyloxy then the reaction is preferably carried out in an inert solvent, such as toluene or dimethylformamide. In this instance, it is preferred that the group Q is $Cl_3CO$— or succinimidyloxy and that the reaction is carried out in toluene at reflux temperature.

When the compound of formula (III) has an imidazolyl NH moiety wherein $R_1/R_2$ is hydrogen, adjacent to the point of attachment of the $QCO(CH_2)$— group, the compound of formula (III) may be of formula (III)':

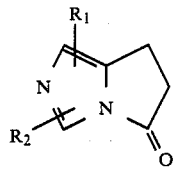  (III)' i.e. a cyclic anhydride.

The conditions for this reaction are similar to those used when Q is $C_{1-4}$ alkoxy.

The present invention also provides a process for the preparation of a compound of formula (I) wherein Z is of sub-formula (c), (d) or (e) or a pharmaceutically acceptable salt thereof, which process comprises reacting a compound of formula (IV):

$Z^2COCH_3$  (IV)

wherein $Z^2$ is of sub-formula (c), (d) or (e), with a compound of formula (V):

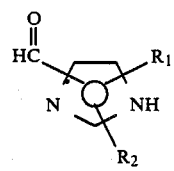  (V)

in the presence of a base (Claisen-Schmidt) reaction followed by reduction of the resulting compound of formula (VI):

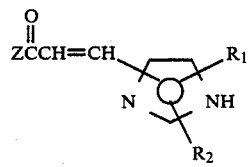  (VI)

wherein the variable groups are as defined in formula (I); and thereafter optionally forming a pharmaceutically acceptable salt thereof.

The Claisen Schmidt reaction takes place in the presence of a base, preferably containing alkoxide or hydroxide ion, for example sodium hydroxide in ethanol as solvent, at ambient temperature.

The reduction is preferably carried out by catalytic hydrogenation using hydrogen-platinum although it may also be carried out using reducing agents, such as sodium borohydride in pyridine.

It will be appreciated that these reduction conditions will probably also reduce the carbonyl group in formula (VI) and therefore it will be necessary to oxidise the resulting alcohol using an appropriate oxidising agent, such as sodium dichromate.

Alternatively, the reduction may be carried out using sodium borohydride in methanol, which reduces only the carbonyl group in formula (VI); the resulting $\alpha\beta$ unsaturated alcohol is then heated under reflux in ethanolic potassium hydroxide to produce the rearranged product of formula (I).

The compounds of formula (II), (III), (IV) and (V) are known or are prepared analogously to, or routinely from, known compounds.

As regards $Z^1$ and $Z^2$ in the compounds of formulae (II) and (IV), reference is hereby made to the following:
(a) EP-A-247266
(b) EP-A-235878
(c) EP-A-255297 and European Patent Application No. 88303336.7
(d) EP-A-200444
(e) UK Patent 2125398 and European Patent Application No. 88303336.7.

(All European Patent References are in the name of Beecham Group p.l.c.).

Pharmaceutically acceptable salts of the compounds of this invention may be formed conventionally. The acid addition salts may be formed for example by reaction of the base compound of formula (I) with a pharmaceutically acceptable organic or inorganic acid.

The compounds of the present invention are 5-HT$_3$ receptor antagonists and it is thus believed may generally be used in the treatment or prophylaxis of emesis, migraine, cluster headaches, trigeminal neuralgia, and visceral pain. Compounds which are 5-HT$_3$ antagonists may also be of potential use in the treatment of CNS disorders such as anxiety and psychosis; drug withdrawal syndrome; arrhythmia; obesity and gastrointestinal disorders such as irritable bowel syndrome.

Antiemetic activity includes in particular that of preventing cytotoxic agent or radiation induced nausea and vomiting. Examples of cytotoxic agents include cisplatin, doxorubicin and cyclophosphamide.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of emesis, migraine, cluster headache, trigeminal neuralgia, visceral pain, gastrointestinal disorders and/or CNS disorders in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 7 kg adult will normally contain 0.05 to 1000 mg for example 0.1 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of emesis, migraine, cluster headache, trigeminal neuralgia, gastrointestinal disorders and/or CNS disorders.

The following Examples illustrate the invention.

DESCRIPTION 1

3-Acetyl-1-methyl indazole (D1)

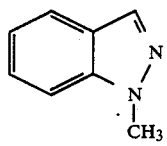 (D1)

A stirred suspension of 1-methylindazole-3-carboxylic acid (8.8 g) in dry Et₂O (200 ml) was cooled to 0° C. and treated with 80 ml of a 1.5M solution of methyl lithium in Et₂O. The reaction mixture was stirred at room temperature for 18 h, poured into 5N HCl/ice (100 ml) and the upper organic layer separated and washed successively with water (50 ml), 2.5N NaOH (50 ml) and brine (50 ml) and finally dried ($K_2CO_3$). Filtration and evaporation afforded the title compound (5.5 g) used without further purification.

$^1$H Nmr (CDCl₃) δ: 8.40–8.12 (m, 1H), 7.42–7.00 (m, 3H), 4.05 (s, 3H), 2.65 (s, 3H).

EXAMPLE 1

N-(3,3-Dimethylindolin-1-yl)-3-(4-imidazolyl)propionamide monohydrochloride (E1)

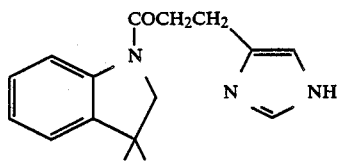 (E1)

A suspension of 3-(4-imidazolyl)propionic acid monohydrochloride (2.0 g) (Chem. Ber. 66, 156 [1933]) in thionyl chloride (10 ml) and DMF (3 drops) was stirred at room temperature for 3 h. The excess thionyl chloride was removed by rotary evaporation and the residue re-evaporated with 2×50 ml of dry toluene. The residue was suspended in $CH_2Cl_2$ (100 ml) and a solution of 3,3-dimethyl indoline (1.7 g) and triethylamine (4 ml) in $CH_2Cl_2$ (50 ml) was added with stirring and cooling. The reaction mixture was stirred overnight, washed with saturated NaHCO₃ and the lower organic layer dried ($Na_2SO_4$). Concentration of the organic extracts afforded the crude product which was purified by column chromatography on silica, eluting with CHCl₃ containing increasing quantities of methanol. The title compound free base was converted to the hydrochloride salt by standard procedures.

m.p. 226°–8° C.

$^1$H Nmr (D⁶-DMSO) δ: 9.11 (s, 1H), 8.15 (d, 1H), 7.58 (s, 1H), 7.36 (d, 1H), 7.27 (t, 1H), 7.13 (t, 1H), 3.99 (s, 2H), 3.05 (br.s, 4H), 1.40 (s, 6H).

Following the procedures outlined in Example 1, the following compounds were prepared.

EXAMPLES 2 TO 5

N-(3,3-Dimethylindolin-1-yl)-3-(5-methyl-4-imidazolyl)propionamide (E2)

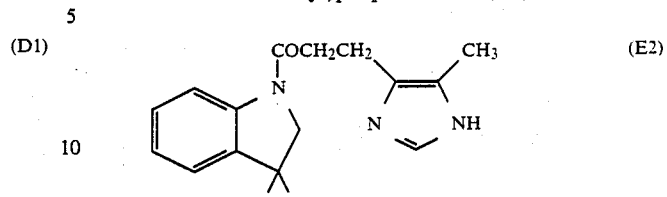 (E2)

m.p. 151°–3° C.

$^1$H Nmr (CDCl₃) δ: 8.22 (d, 1H), 7.42 (s, 1H), 7.26–7.00 (m, 4H), 3.71 (s, 2H), 2.95 (t, 2H), 2.71 (t, 2H), 2.20 (s, 3H), 1.31 (s, 6H).

N-(2-Methoxyphenyl)-3-(5-methyl-4-imidazolyl)propionamide (E3)

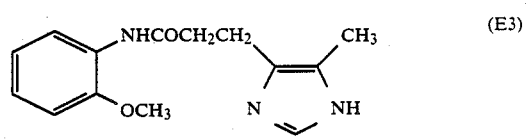 (E3)

m.p. 149°–151° C.

$^1$H-Nmr (d⁶-DMSO) δ 8.65 (brs, 1H), 8.13 (d, 1H), 7.37 (s, 1H), 7.05–6.80 (m, 3H), 3.82 (s, 3H), 2.84 (t, 2H), 2.71 (t, 2H), 2.13 (s, 3H).

N-(2-Methoxyphenyl)-3-(4-imidazolyl)propionamide (E4)

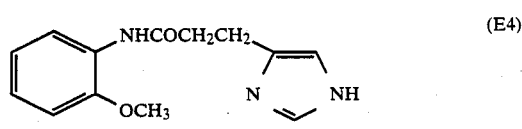 (E4)

m.p. 98°–9° C.

$^1$H Nmr (CDCl₃) δ: 8.32 (d, 1H), 7.90 (brs, 1H), 7.52 (s, 1H), 7.10–6.80 (m, 4H), 3.84 (s, 3H), 3.01 (t, 2H), 2.78 (t, 2H).

3-(5-Methyl-4-imidazolyl)-1-(1-methylindazol-3-yl)propan-1-one (E5)

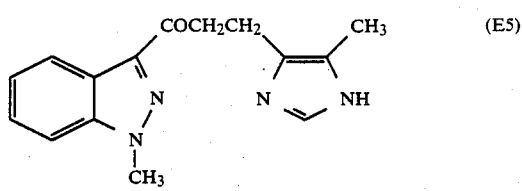 (E5)

A solution of 3-acetyl-1-methylindazole (2.5 g) and 5-methyl-1-(triphenylmethyl)-1-H-imidazole-4-carboxaldehyde (5.25 g) (EP 0,242,973) in t-butanol (200 ml) was stirred and heated to reflux for 1 h with potassium t-butoxide (3.5 g). The cooled reaction mixture was poured into 2N Na₂CO₃ (300 ml) and extracted with $CH_2Cl_2$ (3×150 ml). The combined organic extracts were dried ($K_2CO_3$), filtered and concentrated to give an oil which was purified by column chromatography on silica, eluting with CHCl₃ to give an unsaturated ketone as condensation product (2.8 g) ms. MH⁺ 509. A portion of this product (1.0 g) was suspended in EtOH (100 ml) and hydrogenated at atmospheric pressure/room temperature over 10% Pd/C for 2 days. The catalyst was removed by filtration and the filtrate evaporated to dryness. The residue was heated to reflux at a mixture of acetic acid (10 ml), water (10 ml) and THF (10 ml) for 1 h. The solution was poured into 1N HCl (50 ml) and washed with EtOAc (2×50 ml). The aqueous layer was basified to pH 9 with $K_2CO_3$ and the product extracted into $CH_2Cl_2$ (3×50 ml). The combined organic extracts were dried ($Na_2SO_4$), filtered and evaporated to give an oil which crystallised on treatment with $Et_2O$ (0.2 g). m.p. 152°-4° C.

$^1H$ Nmr (CDCl$_3$) δ: 8.35 (d, 1H), 7.50-7.25 (m, 4H), 4.12 (s, 3H), 3.50 (t, 2H), 3.00 (t, 2H), 2.21 (s, 3H).

PHARMACOLOGY

Antagonism of the von Bezold-Jarisch reflex

The compounds were evaluated for antagonism of the von Bezold-Jarisch reflex evoked by 5-HT in the anaesthetised rat according to the following method:

Male rats 250≧350 g, were anaesthetised with urethane (1.25 g/kg intraperitoneally) and blood pressure and heart rate recorded as described by Fozard J. R. et al., J. Cardiovasc. Pharmacol. 2, 229–245 (1980). A submaximal dose of 5-HT (usually 6 μg/kg) was given repeatedly by the intravenous route and changes in heart rate quantified. Compounds were given intravenously and the concentration required to reduce the 5-HT-evoked response to 50% of the control response ($ED_{50}$) was then determined.

The results are as shown in Table 1.

TABLE 1

| Compound | $ED_{50}$ μg/kg i.v. |
|---|---|
| E1 | 4.2 |

I claim:

1. A compound of formula (I), or a pharmaceutically acceptable salt thereof:

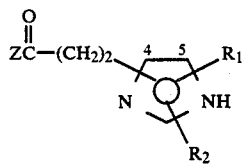

wherein $R_1$ and $R_2$ are independently hydrogen or $C_{1-6}$ alkyl;

Z is a group of sub-formula (a), (b), (c), (d) or (e):

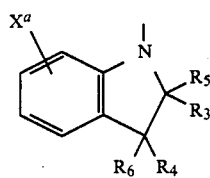

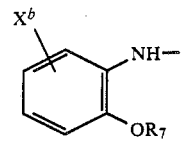

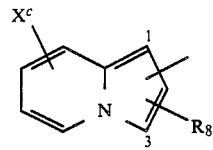

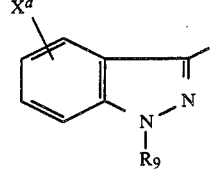

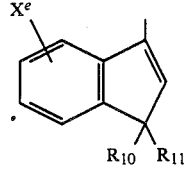

wherein $X^a$ to $X^e$ are selected from hydrogen, halogen and hydroxy;

$R_3$ is hydrogen and $R_4$ is hydrogen or $C_{1-6}$ alkyl;

$R_5$ to $R_{11}$ are independently selected from hydrogen or $C_{1-6}$ alkyl.

2. A compound of formula (I) according to claim 1, wherein Z is of sub-formula (a) and the remaining variables are as defined in claim 1.

3. A compound according to claim 2 wherein $R_3$ and $R_5$ are both hydrogen and one or both of $R_4$ and $R_6$ are alkyl groups as defined in claim 1.

4. A compound of formula (I) according to claim 1, wherein Z is of sub-formula (b) and the remaining variables are as defined in claim 1.

5. A compound according to claim 4 wherein $R_7$ is methyl.

6. A compound selected from the group consisting of
N-(3,3-dimethylindolin-1-yl)-3-(4-imidazolyl)propionamide,
N-(3,3-dimethylindolin-1-yl)-3-(5-methyl-4-imidazolyl)propionamide,
N-(2-methoxyphenyl)-3-(5-methyl-4-imidazolyl)propionamide,
N-(2-methoxyphenyl)-3-(4-imidazolyl)propionamide,
3-(5-methyl-4-imidazolyl)-1-(1-methylindazol-3-yl)propan-1-one,
or a pharmaceutically acceptable salt of any of the foregoing.

7. A pharmaceutical composition for use in treating migraine, cluster headache, trigeminal neuralgia, visceral pain, gastrointestinal disorders and/or CNS disorders in mammals comprising an effective amount of a compound according to claim 1 and a pharmaceutically acceptable carrier.

8. A method of treatment or prophylaxis of migraine, cluster headache, trigeminal neuralgia, visceral pain, gastrointestinal disorders and/or CNS disorders in mammals which comprises the administration of an effective amount of a compound according to claim 1.

* * * * *